United States Patent
Ishitani et al.

(10) Patent No.: US 6,521,743 B1
(45) Date of Patent: Feb. 18, 2003

(54) ANTIBODY AGAINST GLYCERALDEHYDE-3-PHOSPHATE DEHYDROGENASE AND USE THEREOF

(75) Inventors: Ryoichi Ishitani, Saitama (JP); Nobuo Katsube, Osaka (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/807,386

(22) PCT Filed: Oct. 13, 1999

(86) PCT No.: PCT/JP99/05637

§ 371 (c)(1),
(2), (4) Date: Apr. 12, 2001

(87) PCT Pub. No.: WO00/22156

PCT Pub. Date: Apr. 20, 2000

(30) Foreign Application Priority Data

Oct. 13, 1998 (JP) .......................................... 10-290830

(51) Int. Cl.[7] .............................................. C07K 16/40
(52) U.S. Cl. .................. 530/388.26; 435/7.1; 435/7.21; 435/338
(58) Field of Search ....................... 530/388.26; 435/7.1, 435/338, 7.21

(56) References Cited

FOREIGN PATENT DOCUMENTS

JP          8-92127       4/1996   .......... A61K/45/00

OTHER PUBLICATIONS

Ishitani, R, et al, J Neurochem 1996 Mar.; 66 (3): 928–935.*
Tajima, H, et al, Neuroreport 1999 Jul. 13; 10 (10): 20–29–2033.*
Tanaka, R, et al, J Cerebral Blood Flow Metab. 2002; 22: 280–8.*
Database BIOSIS, Accession No. 2001:497477, Fukuhara, Y, et al, Soc Neurosci Abstr 2001; 27 (1): 527.*
Ishitani, R, et al, Mol Pharmacol 1998; 53: 701–707.*
Katsube, N, et al, J Pharmacol Exp Therap 1999, 288 (1): 6–13.*
Ryoichi Ishitani, et al. "Nuclear localization of overxpressed glyceraldehyde–3–phosphate dehydrogenase in cultured cerebellar neurons undergoing apoptosis", Molecular Parmacology (1998, Apr.), vol. 53, No. 4, pp. 701–707.
Katsuyoshi Sunaga, et al. "Glyceraldehyde–3–phosphate dehydrogenase is over–expressed during apoptotic death of neuronal cultures and is recognized by a monoclonal antibody against amyloid plaques from Alzheimer's brain" Neuroscience Letters (1995), vol. 200, No. 2, pp. 135–136.
XP–001038647, Abstract (one page) of: R. Ishitani et al., Overexpression of Glyceraldehyde–3–Phosphate Dehydrogenase (GAPDH) Induce Apoptosis: Generation of Inclusion Bodies By GAPDH–GFP Fusion Protein, vol. 25, No. 1–2, pp. 2274 (1999). Society for neuroscience abstracts.

* cited by examiner

*Primary Examiner*—Anthony C. Caputa
*Assistant Examiner*—Stephen L. Rawlings
(74) *Attorney, Agent, or Firm*—Sughrue Mion, PLLC

(57) ABSTRACT

A novel monoclonal antibody against glyceraldehyde-3-phosphate dehydrogenase (GAPDH), its use and a hybridoma strain NCK-J24 which produces the antibody.

Since the monoclonal antibody produced by the hybridoma of the present invention recognizes GAPDH selectively and strongly, it can be used in screening and diagnosis of an apoptosis-concerning protein and prevention and/or treatment of neurodegenerative diseases (Alzheimer's disease, Parkinson's disease, Parkinson's syndrome, Huntington's disease, Machado-Joseph's disease, amyotrophic lateral sclerosis, Creutzfeldt-Jacob's disease and the like) and GAPDH-concerning diseases (motor dysfunction and the like caused by spinal cord injury, spinal cord compression, cerebral ischemia, peripheral nerve injury and the like).

6 Claims, No Drawings

ANTIBODY AGAINST GLYCERALDEHYDE-3-PHOSPHATE DEHYDROGENASE AND USE THEREOF

TECHNICAL FIELD

The present invention relates to a novel monoclonal antibody against glyceraldehyde-3-phosphate dehydrogenase (abbreviated as GAPDH or G3PD, referred to as GAPDH in this description), use of the antibody and a hybridoma producing the antibody.

More specifically, it relates to a novel antibody against GAPDH which is a killer protein in neuronal cell apoptosis, a hybridoma which produces the antibody and a preparation method thereof, a screening method of an apoptosis-regulating substance using the antibody, a diagnosis method of an apoptosis-participated disease and an agent for preventing and/or treating an apoptosis-participated disease.

BACKGROUND ART

Apoptosis or programmed cell death (planned cell death) is one of the steps of cell death proposed by Kerr, Wyllie et al. (see *Brit. J. Cancer,* 26: 239 (1972)). Apoptosis is found at the time of physiological ontogenesis or expression of diseases and drug effects, and considered to be caused by the activation of a death-inducing program naturally possessed by individual cell. Apoptosis is distinguished from necrosis which means a step in which cells die by damage.

Apoptosis is different from necrosis in that it accompanies RNA synthesis and protein synthesis. These syntheses are not carried out in the case of necrosis.

There are various stimuli which induce apoptosis and the mechanism also has diversity, but morphological characteristics are in common. As a morphological change, formation of chromatin condensation is firstly observed, and fragmentation reaction of DNA is accompanied therewith in almost all cases (see *Nature,* 284: 555 (1980)). It is considered that, when aggregation of chromatin is induced, condensation of cytoplasm and the like occurs, the cell per se forms a cell fragment called apoptotic body, the formed apoptotic body is subjected to phagocytosis degradation by peripheral cells, macrophage and the like, and the apoptosis is completed.

It is known that apoptosis is also concerned in various diseases. For example, HIV virus infection is exemplified. When infected with HIV virus, resistance against the infection disappears due to extinction of lymphocytes, and it is considered that this extinction of lymphocytes is caused by apoptosis in most cases (see *Science,* 257: 217 (1992)).

It is known that the reduction of lymphoid cells is also caused by apoptosis in patients of autoimmune diseases and the like. Also, it has been shown that the extinction of spinal cord cells by apoptosis is also one of the cause of cerebral myelitis as an autoimmune disease in the nervous system.

Furthermore, a relation of learning disability and disturbance of memory to apoptosis is considered to be also important in diseases, such as Alzheimer's disease and the like, which accompany neuron death. With regard to the relationship to cancers, it has been revealed that a tumor suppressor gene p53 is concerned in the apoptosis of DNA-damaged cells, so that participation of tumor suppressor genes in apoptosis is also noticed. In addition, with regard to the relationship to carcinogenesis, it is known that most of the cells which form hyperplastic node as a precancerous tissue die out due to apoptosis, and the remained cells eventually change into cancer cells.

The inventors of the present invention have previously fled a patent application disclosing that GAPDH is a protein which is concerned in apoptosis (JP-A-8-92127). This application describes simultaneously on an antibody against GAPDH, screening of an apoptosis-regulating substance using the antibody, diagnosis of an apoptosis-participated disease and prevention and/or treatment of an apoptosis-participated disease, but the antibody is not described actually.

Furthermore, the inventors of the present invention have previously prepared a monoclonal antibody (called No. 4 antibody) against GAPDH, and reported that GAPDH can be measured using the same (*Molecular Pharmacology,* 53: 701–707 (1998)).

Moreover, the antibody against GAPDH is currently available from Advanced Immuno Chemical and Biogenesis as a catalogue No. RGM2 and a catalogue No. 4699-9555, respectively.

DISCLOSURE OF THE INVENTION

This time, the inventors of the present invention have prepared a novel monoclonal antibody against GAPDH, and found that the antibody recognizes GAPDH specifically and strongly, and thereby accomplished the present invention.

The present invention relates to a monoclonal antibody (produced by a hybridoma strain NCK-J24) against GAPDH which is deeply concerned in the programmed cell death in mammals.

The antibody of the present invention is an excellent antibody which specifically recognizes the protein GAPDH corresponding to apoptosis and has extremely low cross-reacting property with analogous compounds of the protein GAPDH.

The hybridoma strain NCK-J24 capable of producing the monoclonal antibody of the present invention has been deposited on Sep. 9, 1998, in National Institute of Bioscience and Human Technology, Agency of Industrial Science and Technology, the Ministry of International Trade and Industry, Japan (address: Higashi 1-1-3, Tsukuba, Ibaraki, Japan) as the accession number FERM P-16984, and has been transferred to the International Depositary Authority on Oct. 7, 1999, as FERM BP-6912.

DETAILED DESCRIPTION OF THE INVENTION

The monoclonal antibody of the present invention produced by NCK-J24 can be prepared by the following steps (1) to (6).
(1) The apoptosis-corresponding protein GAPDH is used as the immunogen for sensitizing an animal.
(2) Spleen cells of the sensitized animal and myeloma cells derived from the sensitized animal are subjected to cell fusion.
(3) Cells which produce a monoclonal antibody against GAPDH are screened from the thus obtained hybridomas.
(4) A hybridoma which produces the objective antibody is cloned.
(5) The cloned antibody-producing hybridoma is propagated.
(6) The thus produced antibody is separated and purified.
Each of the steps is described specifically.

In the sensitization step (1), it is preferred to administer GAPDH intraperitoneally to the animal to be sensitized. Also, the sensitized animal is not particularly limited, so long as that it is an animal from which a monoclonal antibody is generally obtained, such as mouse, rat or the like. However, a mouse, particularly BALB/c, is used preferably. With regard to dose of the antigen, its administration of from 10 to 200 μg per once is sufficient, for example, in the case of mouse.

The cell fusion of (2) is carried out by excising the spleen from a sensitized animal having a sufficiently increased antibody titer, among the sensitized animals immunized in the step (1), preparing a suspension of spleen cells in the usual way, and then adding polyethylene glycol (preferably PEG 4000) at 37° C. to a mixture of the thus obtained spleen cells and myeloma cells derived from the sensitized animal. As the mouse myeloma cells, several kinds, such as P3x63Ag8, P3/N00S1/1-Ag4-1, SP-2/0-Ag-14 and the like, are known, and all of them are easily available.

As the myeloma cells, an HGPRT (hypoxanthine-guanine phosphoribosyl transferase)-defective cell strain which cannot survive in HAT medium (a medium containing hypoxanthine, aminopterin and thymidine) is useful, and it is more preferred that it is a cell strain in which the myeloma cells themselves do not secrete the antibody. Preferably, SP-2/0-Ag-14 is used.

Next, the thus obtained cell fusion mixture is dispensed into a 96 micro-well plate at a low cell density and cultured using HAT medium. By culturing them for 1 to 2 weeks, un-fused myeloma cells, hybridomas of myeloma cells themselves, un-fused spleen cells and hybridomas of spleen cells themselves die out because their surviving conditions are not satisfied, and only the hybridomas of spleen cells with myeloma cells are propagated.

In the screening of (3), whether or not the hybridoma is hybridoma which produces an antibody against the antibody against GAPDH is judged by allowing each hybridoma culture supernatant to react with the antibody against GAPDH, separating antibody fractions and then determining the amount of a labeled substance in each antibody fraction, or by allowing each hybridoma culture supernatant to react with the immobilized antigen and determining amount of the antibody in the supernatant specifically adsorbed to the antigen, using a labeled second antibody.

The step (4) is carried out by cloning the antibody-producing hybridoma in accordance with the soft agar method (*Monoclonal Antibodies*, p. 372 (1980)). In this case, it is possible to use the limiting dilution analysis.

The step (5) is carried out by culturing the cloned hybridoma using a usually used medium and then separating and purifying from the culture supernatant, but a method in which the hybridoma is administered into the abdominal cavity of mouse, allowed to propagate therein and then separated and purified from the ascites is used for obtaining a larger amount of the antibody efficiently.

In the step (6), the purification can be carried out by usually used methods such as salting out, ion exchange chromatography, gel filtration, hydrophobic chromatography, affinity chromatography and the like, but an affinity chromatography using protein A-Sepharose CL-4B (manufactured by Pharmacia) is used more effectively.

INDUSTRIAL APPLICABILITY

The antibody of the present invention produced by hybridoma strain NCK-J24 is an excellent antibody which specifically recognizes GAPDH and has extremely low cross-reacting property with analogous compounds of GAPDH.

Since the antibody of the present invention specifically recognizes GAPDH, it can be used in the purification and concentration of GAPDH, for example, in affinity chromatography and the like.

However, the most important application method of the antibody of the present invention is application to an immunological determination method of the protein GAPDH, which is excellent in accuracy and detection limit.

In the determination method of the present invention, body fluids (blood, urine, cerebrospinal fluid, and the like) and the like are used as samples to be tested.

As the diseases in which apoptosis is concerned, neurodegenerative diseases (Alzheimer's disease, Parkinson's disease, Parkinson's syndrome, Huntington's disease, Machado-Joseph's disease, amyotrophic lateral sclerosis, Creutzfeldt-Jacob's disease, and the like) are included. Also, as the diseases in which GAPDH is concerned, motor dysfunction and the like caused by spinal cord injury, spinal cord compression, cerebral ischemia, peripheral nerve injury and the like are included.

Application for Pharmaceuticals

For the purpose above described, the monoclonal antibody produced by the strain NCK-J24 of the present invention may be normally administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 μg and 1000 μg, by oral administration, up to several times per day, and between 1 μg and 300 μg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavouring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution, plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOLBATE80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or 3,095,355 may be used.

Furthermore, the monoclonal antibody produced by the strain NCK-J24 of the present invention can be used for study of relationship between GAPDH and diseases, diagnosis of diseases and the like by determining GAPDH. Moreover, the monoclonal antibody of the present invention can be used as it is, in the form of a chimeric antibody with a human antibody or in the form of a humanized antibody as a preventive and/or treating agent.

The monoclonal antibody of the present invention produced by the strain NCK-J24 can be applied to Western blotting, immunofluorescence technique or immunoelectron microscopic analysis. As a result of Western blotting, GAPDH corresponding to 38 kDa is specifically recognized. As a result of immunofluorescence technique or immunoelectron microscopic analysis, said antibody strongly and specifically recognizes staining ability of membrane-binding type GAPDH on the nucleus, which is over-expressed at the time of apoptosis.

Since GAPDH is concerned in apoptosis, it can also be used for the screening and the like of substances concerned in apoptosis by measuring expression of said polypeptide.

BEST MODE FOR CARRYING OUT THE INVENTION

The present invention is explained below in detail with reference to Examples; however, they do not restrict the scope of the present invention.

EXAMPLE 1

Preparation of Antigen for Sensitization

A) Preparation of Primary Culture Neuronal Cell (CGC)

Based on the method of Ishitani et al., CGC was prepared in the following manner (Ishitani et al., *J. Neurochem.*, 66: 928–35, 1996).

The cerebellum was excised from a Sprague-Dawley rat of 8 days of age and made into 0.4 mm square sections using a McIlwain tissue chopper. Thereafter, digestion was carried out at 37° C. for 15 minutes in 0.025% trypsin-containing Krebs-phosphate buffer.

After termination of the reaction with 0.008% soybean trypsin inhibitor and 0.0016% deoxyribonuclease I-containing Krebs-phosphate buffer, dispersed neuronal cells were obtained by carrying out trituration with a tapering Pasteur pipette in Krebs-phosphate buffer containing 0.01% deoxyribonuclease I and 0.05% soybean trypsin inhibitor.

These cells were suspended in modified Eagle's medium containing 10% fetal calf serum, 2 mM glutamine, 50 $\mu$g/ml gentamicin and 25 mM potassium chloride and inoculated into a plastic dish (35 mm) coated with poly-L-lysine (molecular weight 3 to $7\times10^4$, 100 $\mu$g/ml) at a cell density of $2.1\times10^5$ intact cells/cm$^2$.

The culturing was started at 37° C. in an atmosphere of 5% carbon dioxide, cytosine arabinofuranoside (10 $\mu$M) was added 18 to 24 hours thereafter for the purpose of inhibiting growth of non-neuronal cells and the culturing was continued.

B) Preparation of Antigen (GAPDH)

Cells were recovered from the medium cultured for 17 days, using 50 mM Tris-HCl buffer (pH 7.4). The cell suspension was subjected to ultra sonic treatment and the thus obtained homogenate was centrifuged at $2\times10^5$ G for 30 minutes. The membrane fraction suspension obtained in this manner was mixed with SDS-PAGE sample buffer at a ratio of 1:1 to adjust the final protein concentration to 3 mg/ml. A 15 $\mu$l portion of this sample was allowed to stand overnight at 4° C. and then SDS-PAGE was carried out under the following conditions:

Gel used: No. 01-003 SDS-PAGE mini 12% (1.5 mm, 15 wells) manufactured by Tefco

Electrophoresis vessel: No. 03-001 manufactured by Tefco

Electrophoresis condition: 150 V, 90 minutes.

After the electrophoresis, the gel was stained for 2 to 3 minutes with 0.1% Coomassie Brilliant Blue R-250 in 1% acetic acid and 40% methanol. This was then decolorized with 10% methanol for about 60 minutes until bands became clear.

After washing with distilled water, the band of interest (38 kDa) was cut out. The thus cut-out band was homogenized and used as the antigen.

EXAMPLE 2

Sensitization of Mouse and Preparation of Hybridoma

The antigen obtained in Example 1 (30 $\mu$g) was suspended in Laemili sample buffer and allowed to stand overnight at 4° C. The suspension was administered into the abdominal cavity of BALB/c mouse (two animals) using a syringe, and booster was carried out 2 weeks and 4 weeks thereafter. Blood samples were collected after 3 weeks and 5 weeks and the antibody titer was measured by ELISA. When the antibody titer reached plateau, spleen cells of one mouse having higher antibody titer was subjected to cell fusion using a myeloma strain NS-1 for hybridoma use (Kurabo) in the usual way.

EXAMPLE 3

Screening of Hybridoma

The hybridoma fused cells prepared in Example 2 were inoculated into 360 well polyethylene microplate and first screening was carried out by ELISA. A total of 22 wells having high antibody titers were selected therefrom. They were again subjected to second screening and 7 wells were selected. Hybridoma cells of the 7 wells were again cultured, and the thus obtained hybridoma cells were checked for the antibody specificity by SDS-PAGE to obtain monoclones. As a result, 3 positive clones were obtained.

EXAMPLE 4

Preparation of Antibody

A) Culturing of Hybridoma

The three hybridomas obtained in Example 3 were cultured using PRMI medium containing 15% FCS (Monoclonal Antibodies, p.372 (1980)). After sufficient culturing, the number of cells was counted and the cells were suspended in serum-free PRMI 1640 medium. Using a syringe, 0.2 ml ($2 \times 10^6$ cells) of the suspension was transplanted into the abdominal cavity of BALB/c mouse (5 animals) in the usual way.

B) Collection of Ascites

When about 1 to 3 weeks passed after the inoculation of hybridom a cells, ascites was collected from ascites-accumulated mouse one by one. Bloody ascites and cloudy ascites were not found. Among the three hybridomas, two showed markedly low production of ascites.

C) Purification of Antibody

The thus obtained ascites (6.3 ml) accumulated by one hybridoma was fractionated with 50% saturated ammonium sulfate, purified by an affinity chromatography using protein A-Sepharose CL4B column (manufactured by Pharmacia) and then freeze-dried to obtain the antibody of the present invention having an antibody concentration of 1.0 mg/ml. A hybridoma strain NCK-J24 capable of producing this antibody was cultured and frozen. This hybridoma has been deposited on Sep. 9, 1998, in National Institute of Bioscience and Human Technology, Agency of Industrial Science and Technology, the Ministry of International Trade and Industry, Japan, as the accession number FERM P-16984, and has been transferred to the International Depository Authority on Oct. 7, 1999, as FERM BP-6912.

EXAMPLE 5

Analysis of Monoclonal Antibody Produced by NCK-J24

A) SDS-PAGE Analysis

Using the GAPDH obtained in Example 1-B) and a commercially available GAPDH (fowl muscle-derived GAPDH, Sigma Chemical Co., St. Louis, Mo.) and in accordance with the method of Laemili (Nature, 227: 680–685, 1970), mixed with the same volume of 2×Laemili sample buffer (125 mM Tris-HCl buffer (pH 6.8) containing 20% glycerol, 4% SDS, 10% 2-mercaptoethanol and 0.005% Bromophenol Blue) and heat-denatured at 100° C. for 5 minutes. Electrophoresis of the sample was carried out with 8 to 16% linear gradient polyacrylamide gel (manufactured by Tefco) at a constant current of 18 mA and using a Tris-glycine buffer (25 mM tris, 192 mM glycine, 0.1% SDS) as the electrophoresis buffer. The gel after electrophoresis was stained with 0.1% Coomassie Blue. Quantitative analysis of the amount of protein band was carried out by a CCD type image analyzer (BIOPROFIL, N & S).

B) Western Blotting Analysis

After carrying out the SDS-PAGE analysis of insoluble fraction protein in A), electroblotting on a polyvinylidene difluoride (PVDF) membrane (POLYSCREEN, DuPont-New England Nuclear, Boston, Mass.) was carried out. The PVDF membrane after transfer was subjected to 60 minutes of blocking in a TBS-T solution (20 mM Tris-HCl buffer, 137 mM sodium chloride, 0.05% Tween 20, pH 7.4) containing 10% skimmed milk and then 60 minutes of the reaction was carried out in TBS-T comprising primary antibody at room temperature.

As the primary antibody, two types of commercially available antibodies (1.6 $\mu$g/ml), No. 4 antibody and the monoclonal antibody of the present invention produced by NCK-J24 (0.1 $\mu$g/ml and 0.03 $\mu$g/ml) were used.

After washing with the TBS-T solution, the reaction with a secondary antibody (peroxidase-conjugated rabbit anti-mouse Ig antiserum, Daco, Glostrup, Denmark) was carried out in the same manner. After washing the PVDF membrane, detection of bands on a high sensitivity X-ray film was carried out using a chemiluminescence detection reagent (RENAISSANCE, DuPont-New England Nuclear, Boston, Mass.).

Results

As a result of the Western blotting analysis, the monoclonal antibody of the present invention produced by NCK-J24 was confirmed as a band of 38 kDa which is the molecular weight of the standard GAPDH, at a concentration of 0.03 $\mu$g/ml. On the contrary, the band of No. 4 antibody was confirmed at a concentration of 5 $\mu$g/ml, but the band was not found at 0.5 $\mu$g/ml.

Also, since the two types of commercially available monoclonal antibodies (RGM2 from Advanced Immuno Chemical and 4699-9555 from Biogenesis) recognize many molecular species, a large number of bands were found in addition to the 38 kDa band of interest.

EXAMPLE 6

Analysis of Immunoglobulin Subclass of the Monoclonal Antibody of the Present Invention Produced by NCK-J24

Screening of subclass of the monoclonal antibody of the present invention produced by NCK-J24 was carried out using a mouse hybridoma subtyping kit (Boehringer-Mannheim Corp., catalogue No. 1183117). As a result, the class of the antibody of the present invention was IgM.

What is claimed is:

1. A monoclonal antibody against glyceraldehyde-3-phosphate dehydrogenase produced by a hybridoma strain NCK-J24 (FERM BP-6912).

2. A hybridoma strain NCK-J24 (FERM BP-6912).

3. A method for determining the presence of glyceraldehyde-3-phosphate dehydrogenase (GAPDH) in a sample, wherein said method comprises:

(a) contacting said sample with the antibody of claim 1; and (b) detecting the complex of the antibody and GAPDH, thereby determining the presence of GAPDH in the sample.

4. The method of claim 3 wherein said sample is a bodily fluid.

5. The method of claim 4 wherein said bodily fluid is selected from the group consisting of blood, urine, and cerebrospinal fluid.

6. The method of claim 3 wherein said sample is a cell homogenate.

* * * * *